(12) United States Patent
Morgan et al.

(10) Patent No.: US 6,809,507 B2
(45) Date of Patent: Oct. 26, 2004

(54) IMPLANTABLE SENSOR ELECTRODES AND ELECTRONIC CIRCUITRY

(75) Inventors: Wayne A. Morgan, Northridge, CA (US); David Choy, San Gabriel, CA (US); John C. Gord, Venice, CA (US); Rajiv Shah, Rancho Palos Verdes, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

(21) Appl. No.: 10/034,338

(22) Filed: Dec. 28, 2001

(65) Prior Publication Data

US 2003/0076082 A1 Apr. 24, 2003

Related U.S. Application Data

(60) Provisional application No. 60/335,652, filed on Oct. 23, 2001.

(51) Int. Cl.[7] ............................ G01N 27/00; A61B 5/00
(52) U.S. Cl. ...................... 324/71.1; 324/658; 600/347; 204/403.14
(58) Field of Search ................................ 324/71.1, 658, 324/666, 670, 676, 680, 717; 600/300, 301; 307/2, 60; 204/403.14

(56) References Cited

U.S. PATENT DOCUMENTS

| 3,716,059 | A | * | 2/1973 | Welborn et al. ............... 607/4 |
| 3,728,622 | A | * | 4/1973 | Williams .................... 324/71.1 |
| 3,992,665 | A | * | 11/1976 | Preikschat .................. 324/666 |
| 4,240,438 | A | | 12/1980 | Updike et al. |
| 4,333,377 | A | * | 6/1982 | Niezgoda et al. ............. 84/627 |
| 4,479,796 | A | | 10/1984 | Kallok |
| 4,484,987 | A | | 11/1984 | Gough |
| 4,533,986 | A | * | 8/1985 | Jones ........................... 363/7 |
| 4,568,335 | A | | 2/1986 | Updike et al. |
| 4,628,928 | A | | 12/1986 | Lowell |
| 4,650,547 | A | | 3/1987 | Gough |
| 4,703,756 | A | | 11/1987 | Gough et al. |
| 4,757,022 | A | | 7/1988 | Shults et al. |
| 4,771,772 | A | | 9/1988 | DeWitt |
| 4,816,713 | A | * | 3/1989 | Change, Jr. ................. 310/319 |
| 4,890,620 | A | | 1/1990 | Gough |
| 4,900,405 | A | * | 2/1990 | Otagawa et al. ............ 205/781 |
| 4,911,168 | A | | 3/1990 | Davis |
| 4,994,167 | A | | 2/1991 | Shults et al. |
| 5,040,533 | A | * | 8/1991 | Fearnot ....................... 128/419 |
| 5,094,951 | A | | 3/1992 | Rosenberg |
| 5,266,688 | A | | 11/1993 | Rosenberg |
| 5,328,460 | A | | 7/1994 | Lord et al. |
| 5,394,095 | A | * | 2/1995 | Kespohl ...................... 324/674 |
| 5,497,772 | A | | 3/1996 | Schulman et al. |

(List continued on next page.)

FOREIGN PATENT DOCUMENTS

WO    WO 01/01851 A1    11/2001

OTHER PUBLICATIONS

PCT International Search Report as issued in International Application No. PCT/US02/30945, Mailing date Mar. 14, 2003.

Primary Examiner—Anjan Deb
Assistant Examiner—Timothy J. Dole
(74) Attorney, Agent, or Firm—Foley & Lardner LLP

(57) ABSTRACT

An electronic circuit for sensing an output of a sensor having at least one electrode pair and circuitry for obtaining and processing the sensor output. The electrode pair may be laid out such that one electrode is wrapped around the other electrode in a U-shaped fashion. The electronic circuitry may include, among other things, a line interface for interfacing with input/output lines, a rectifier in parallel with the line interface, a counter connected to the line interface and a data converter connected to the counter and the electrode pair. The data converter may be a current-to-frequency converter. In addition, the rectifier may derive power for the electronic circuit from communication pulses received on the input/output lines.

40 Claims, 8 Drawing Sheets

U.S. PATENT DOCUMENTS

| | | | |
|---|---|---|---|
| 5,534,025 A | | 7/1996 | Moussy |
| 5,556,421 A | * | 9/1996 | Prutchi et al. ................. 607/36 |
| 5,593,852 A | | 1/1997 | Heller et al. |
| 5,660,163 A | | 8/1997 | Schulman et al. |
| 5,667,983 A | | 9/1997 | Abel et al. |
| 5,696,314 A | | 12/1997 | McCaffrey et al. |
| 5,707,502 A | | 1/1998 | McCaffrey et al. |
| 5,711,868 A | | 1/1998 | Maley et al. |
| 5,728,281 A | | 3/1998 | Holmstrom et al. |
| 5,741,211 A | | 4/1998 | Renirie et al. |
| 5,741,319 A | | 4/1998 | Woloszko et al. |
| 5,770,028 A | | 6/1998 | Maley et al. |
| 5,773,270 A | | 6/1998 | D'Orazio et al. |
| 5,791,344 A | | 8/1998 | Schulman et al. |
| 5,804,048 A | | 9/1998 | Wong et al. |
| 5,917,346 A | | 6/1999 | Gord |
| 5,919,216 A | | 7/1999 | Houben et al. |
| 5,932,175 A | | 8/1999 | Knute et al. |
| 5,941,906 A | | 8/1999 | Barreras, Sr. et al. |
| 5,965,380 A | | 10/1999 | Heller et al. |
| 5,985,129 A | | 11/1999 | Gough et al. |
| 5,992,211 A | | 11/1999 | Skrtic |
| 5,999,848 A | * | 12/1999 | Gord et al. ..................... 607/2 |
| 5,999,849 A | | 12/1999 | Gord et al. |
| 6,001,067 A | | 12/1999 | Shults et al. |
| 6,002,954 A | | 12/1999 | Van Antwerp et al. |
| 6,027,479 A | | 2/2000 | Alei et al. |
| 6,049,727 A | | 4/2000 | Crothall |
| D424,696 S | | 5/2000 | Ray et al. |
| D426,638 S | | 6/2000 | Ray et al. |
| 6,093,167 A | | 7/2000 | Houben et al. |
| 6,103,033 A | | 8/2000 | Say et al. |
| 6,120,676 A | | 9/2000 | Heller et al. |
| 6,122,536 A | | 9/2000 | Sun et al. |
| 6,125,290 A | | 9/2000 | Miesel |
| 6,125,291 A | | 9/2000 | Miesel et al. |
| 6,134,459 A | | 10/2000 | Roberts et al. |
| 6,135,978 A | | 10/2000 | Houben et al. |
| 6,144,866 A | | 11/2000 | Miesel et al. |
| 6,159,240 A | | 12/2000 | Sparer et al. |
| 6,162,611 A | | 12/2000 | Heller et al. |
| 6,163,723 A | | 12/2000 | Roberts et al. |
| 6,175,752 B1 | | 1/2001 | Say et al. |
| 6,198,952 B1 | | 3/2001 | Miesel |
| 6,201,980 B1 | | 3/2001 | Darrow et al. |
| 6,248,080 B1 | | 6/2001 | Miesel et al. |
| 6,251,260 B1 | | 6/2001 | Heller et al. |
| 6,261,280 B1 | | 7/2001 | Houben et al. |
| 6,268,161 B1 | | 7/2001 | Han et al. |
| 6,387,048 B1 | * | 5/2002 | Schulman et al. .......... 600/300 |
| 2003/0057970 A1 | * | 3/2003 | Shiraki et al. .............. 324/722 |

* cited by examiner

IMPLANTABLE SENSOR ELECTRODES AND ELECTRONIC CIRCUITRY

CROSS-REFERENCE TO RELATED APPLICATIONS

Embodiments of the present invention claim priority from a U.S. Provisional Application entitled "Implantable Sensor Electrodes and Electronic Circuitry," Ser. No. 60/335,652, filed Oct. 23, 2001, the contents of which are incorporated by reference herein.

BACKGROUND

1. Field of the Invention

The present invention relates to the field of sensor electronics and, in particular, to implantable sensor electrodes and implantable electronic circuits for sensors.

2. Description of Related Art

The development of sensors that can survive for extended periods in less than ideal environments has increased the burden on associated electronics used to obtain and process signals received from such sensors. For example, in the medical device field, physiological parameter sensors are available that may be implanted in vivo and left in an in vivo environment for six months to a year and longer. Such extended lengths of time in an in vivo environment have taxed previously available electronic circuitry used in connection with the physiological parameter sensors.

In addition, the availability of physiological parameter sensors that may be placed in a vascular environment or other environment that may subject a physiological parameter sensor to constant fluid environments has increased the burden on electrodes used in conjunction with a biomolecule that may be part of the physiological parameter sensor. Because multiple electrodes may be used in physiological parameter sensing applications, fluids such as, for example, blood, may create multiple conductive paths across electrodes that compromise the integrity of measurements being made with the electrodes. Electrode configuration and associated circuitry known up to this point have been ill-equipped to handle the demands of such an environment.

Moreover, the extended periods of time in which a physiological parameter sensor may be implanted in vivo have placed extra demands on the power sources driving the sensor electrodes and sensor electronics. For example, previous sensor technology, which may have been designed for relatively short term in vivo implantation of a sensor, may have included a power source, such as, for example, a lithium battery, for in vivo implantation along with the sensor. Such short term sensors may have been designed, for example, for emergency use in surgical applications where the intent was to keep the sensor powered even in storage. Thus, a hospital could store the sensors, implant them during emergency surgery, and expect to get sensor readouts immediately. However, with the advent of sensors for long term in vivo implantation, storing a sensor with an activated power source may deplete the power source to such an extent that using the sensor for long term in vivo implantation may be impractical and even unadvisable.

In addition, the demand for enhanced in vivo signal processing has put even greater demands on an already overburdened in vivo power source. Implantable, in vivo automated systems require not only extended term power requirements for powering an implanted power sensor, but also require increased power availability for the circuitry used to obtain and process sensor signals.

SUMMARY OF THE DISCLOSURE

Embodiments of the present invention relate to sensor electrodes and sensor electronics interfaced to the sensor electrodes.

Embodiments of the present invention include an electronic circuit for sensing an output of a sensor including at least one electrode pair for sensing a parameter. The at least one electrode pair may have a first electrode and a second electrode, wherein the first electrode wraps around the second electrode. The electronic circuit may contain circuitry for processing the parameter. The parameter sensed by the electrode pair may be a physiological parameter such as, for example, glucose or oxygen.

The first electrode may wrap around the second electrode in a U-shaped fashion or may surround three sides of the second electrode. The layout of the first electrode and a second electrode may be such that it minimizes cross coupling between the first electrode and the second electrode.

The electronic circuit may include a reference electrode for setting a reference voltage for the at least one electrode pair. The reference voltage may be set to about 0.5 volts.

In addition, the circuitry may include a line interface for interfacing with input/output lines; a rectifier in parallel with the line interface; a counter connected to the line interface; and a data converter connected to the counter and the at least one electrode pair. Control logic may be connected to the counter and the line interface. The control logic may include a state machine and a state decoder connected to the state machine. The control logic may include a microprocessor.

In the electronic circuit, the rectifier may transfer power from communication pulses to a capacitor. The capacitor may power the electronic circuit using power stored from the communication pulses.

The data converter may be an analog-to-digital converter, a voltage-to-frequency converter, or a current-to-frequency converter. If the data converter is a current-to-frequency converter, an output of the current-to-frequency converter may be scaled using a prescaler before connecting to the counter. The prescaler may be a divide-by-16 prescaler.

The circuitry may also include a temperature sensor for reading a temperature of an environment and a voltage reference for applying a voltage to a reference electrode. In addition, switched capacitor circuits may be used as resistors in the electronic circuit.

These and other objects, features, and advantages of embodiments of the invention will be apparent to those skilled in the art from the following detailed description of embodiments of the invention when read with the drawings and appended claims.

DETAILED DESCRIPTION

In the following description of preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the preferred embodiments of the present invention.

Figure 1:
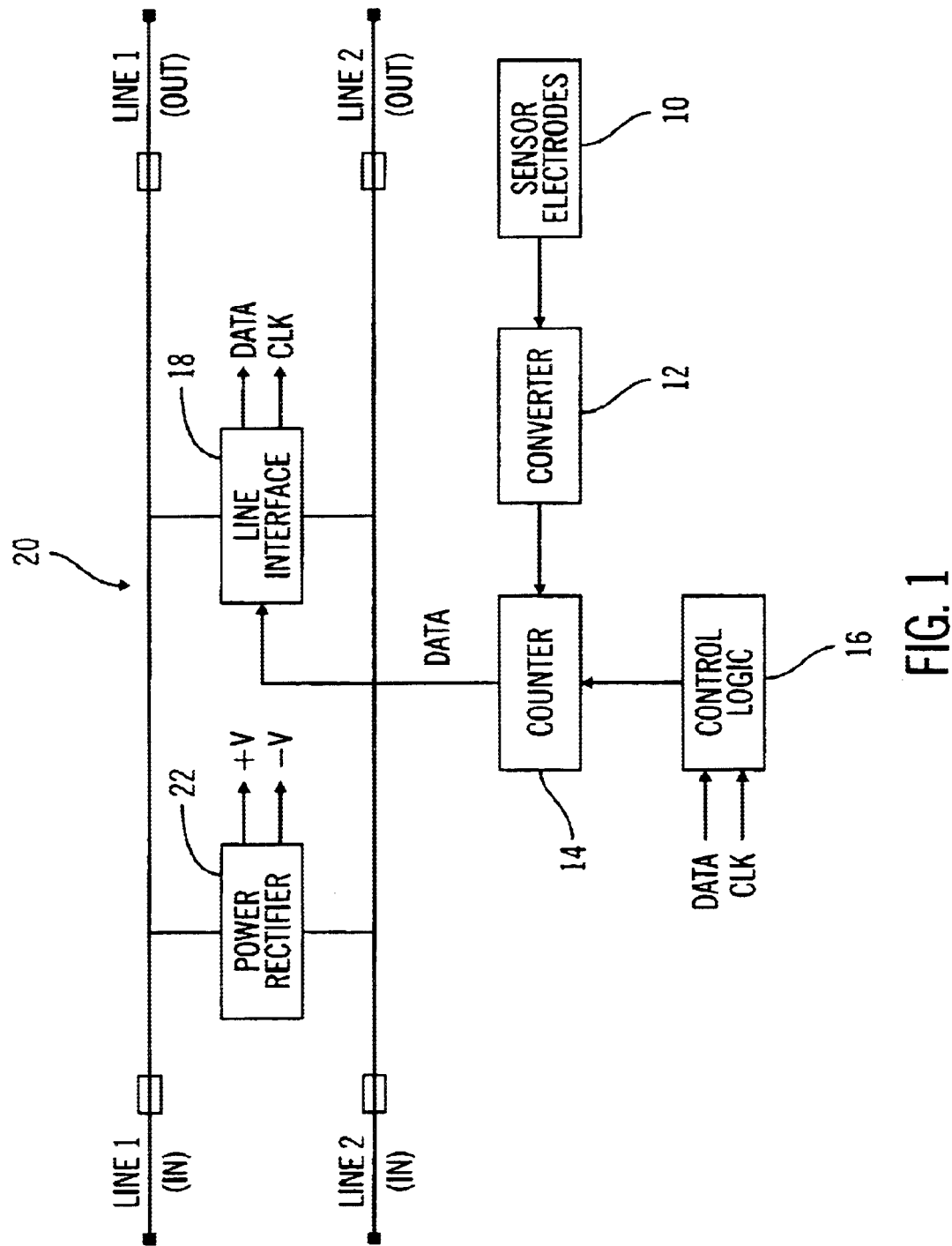
FIG. 1 shows a general block diagram of an electronic circuit for sensing an output of a sensor according to an embodiment of the present invention.

FIG. 1 shows a general block diagram of an electronic circuit for sensing an output of a sensor according to an embodiment of the present invention. At least one pair of sensor electrodes 10 may interface to a data converter 12, the output of which may interface to a counter 14. The counter 14 may be controlled by control logic 16. The output of the counter 14 may connect to a line interface 18. The line interface 18 may be connected to input and output lines 20 and may also connect to the control logic 16. The input and output lines 20 may also be connected to a power rectifier 22.

The sensor electrodes 10 may be used in a variety of sensing applications and may be configured in a variety of ways. For example, the sensor electrodes 10 may be used in physiological parameter sensing applications in which some type of biomolecule is used as a catalytic agent. For example, the sensor electrodes 10 may be used in a glucose and oxygen sensor having a glucose oxidase enzyme catalyzing a reaction with the sensor electrodes 10. The sensor electrodes 10, along with a biomolecule or some other catalytic agent, may be placed in a human body in a vascular or non-vascular environment. For example, the sensor electrodes 10 and biomolecule may be placed in a vein and be subjected to a blood stream, or may be placed in a subcutaneous or peritoneal region of the human body.

Figure 2:
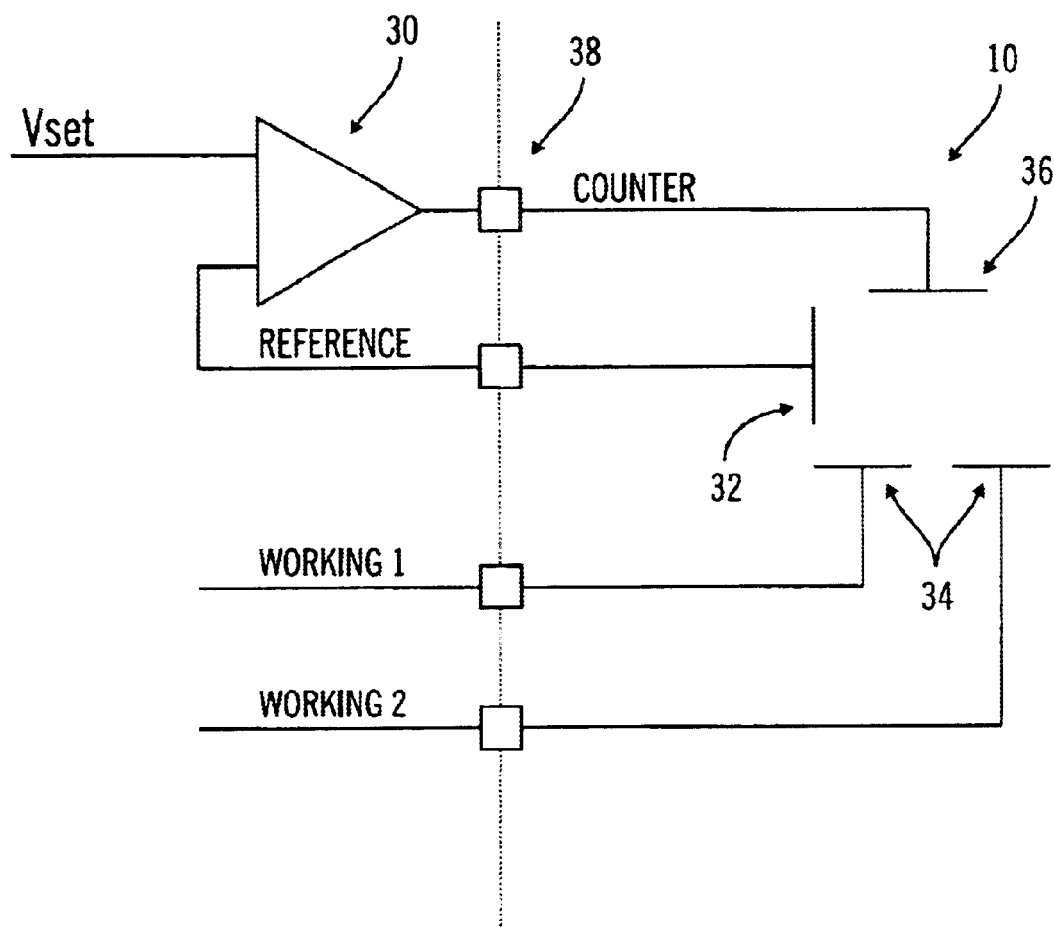
FIG. 2 shows an electronic configuration of the sensor electrodes according to an embodiment of the present invention.

FIG. 2 shows an electronic configuration of the sensor electrodes 10 according to an embodiment of the present invention. An op amp 30 or other servo controlled device may connect to sensor electrodes 10 through a circuit/electrode interface 38. The op amp 30 may attempt to maintain a positive voltage between a reference electrode 32 and a working electrode 34 by adjusting the voltage at a counter electrode 36. According to an embodiment of the present invention, the voltage applied at an input of the op amp 30 and thus set at the reference electrode 32 may be approximately 0.5 volts. Current may then flow from a counter electrode 36 to a working electrode 34. Such current may be measured to ascertain the electrochemical reaction between the sensor electrodes 10 and the biomolecule of a sensor that has been placed in the vicinity of the sensor electrodes 10 and used as a catalyzing agent.

Figure 3:
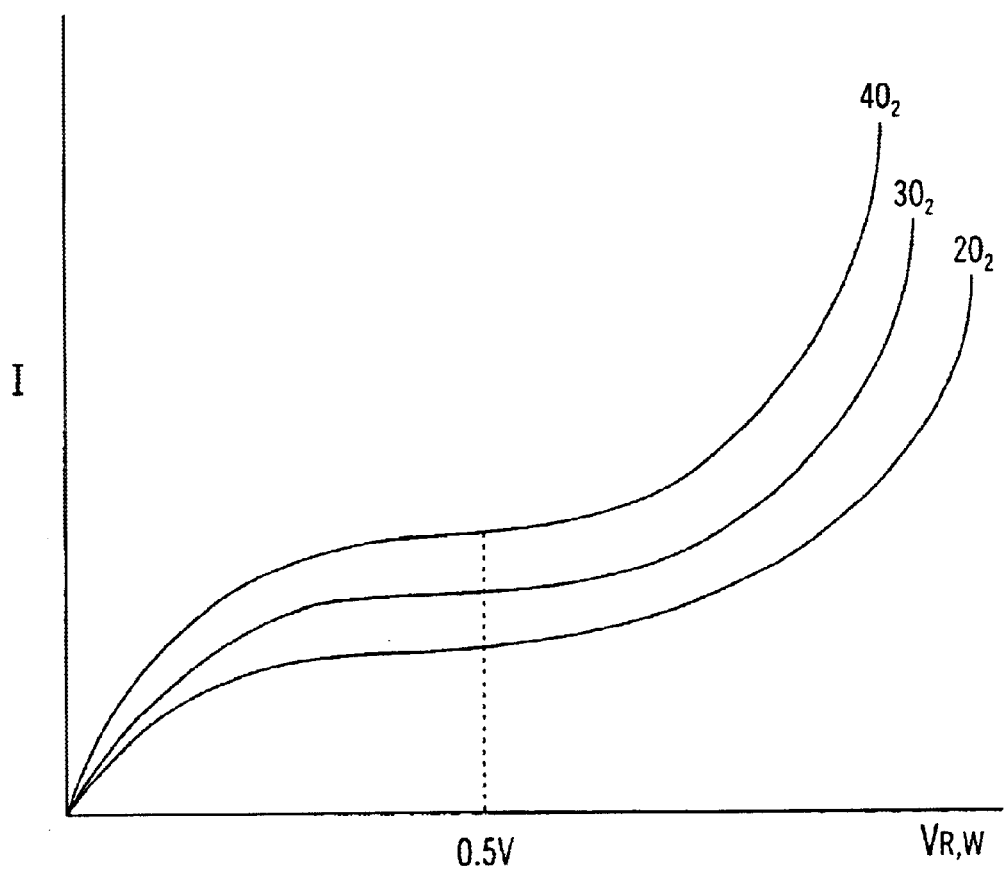
FIG. 3 shows a graph of current versus voltage for varying levels of oxygen according to an embodiment of the present invention.

In an embodiment of the present invention where a glucose oxidase enzyme is used as a catalytic agent in a sensor, current may flow from a counter electrode 36 to a working electrode 34 only if there is oxygen in the vicinity of the enzyme and the sensor electrodes 10. If the voltage set at the reference electrode 32 is maintained at about 0.5 volts, the amount of current flowing from a counter electrode 36 to a working electrode 34 has a fairly linear relationship with unity slope to the amount of oxygen present in the area surrounding the enzyme and the electrodes. Thus, increased accuracy in determining an amount of oxygen in the blood may be achieved by maintaining the reference electrode 32 at about 0.5 volts and utilizing this region of the current-voltage curve for varying levels of blood oxygen. A graph of current versus voltage for varying levels of oxygen may be seen in FIG. 3. Different embodiments of the present invention may utilize different sensors having biomolecules other than a glucose oxidase enzyme and may, therefore, have voltages other than 0.5 volts set at the reference electrode.

According to an embodiment of the present invention, more than one working electrode 34 may be used. However, although current may normally flow out of the op amp 30 toward the counter electrode 36 and then toward a corresponding working electrode 34, in some applications where more than one working electrode 34 is used, current from a counter electrode 36 may be coupled to an unintended working electrode 34. This phenomenon may occur because some environments in which the sensor may be used may provide multiple conductive paths from a counter electrode 36 to any of a plurality of working electrodes 34. For example, when a sensor having a glucose oxidase enzyme is used in glucose and oxygen sensing applications and is placed in a vascular environment, blood surrounding the sensor may create a conductive path from a counter electrode 36 to any of a plurality of working electrodes 34. Current passing through any electrode may generate oxygen at that electrode via electrochemical reaction. Thus, current passing from a counter electrode 36 to an unintended working electrode 34 may generate oxygen at that working electrode 34 and, consequently, give the impression that the oxygen at that working electrode 34 is the result of a reaction between oxygen in the blood and the glucose oxidase enzyme, ultimately resulting in false glucose readings. Such false readings could prove detrimental to a patient relying on such readings for an accurate, automatic injection of insulin into the bloodstream. Accordingly, the sensor electrodes 10 may be configured to minimize the effect of cross coupling between counter electrodes 36 and working electrodes 34.

Figure 4:
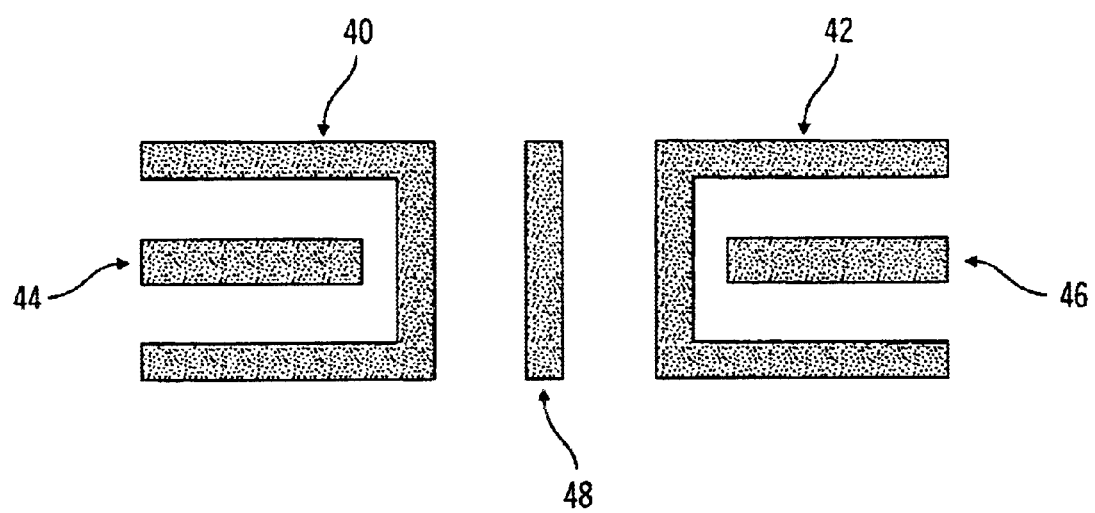
FIG. 4 shows a physical electrode layout to minimize the effect of cross coupling between counter electrodes and working electrodes according to an embodiment of the present invention.

FIG. 4 shows a physical electrode layout to minimize the effect of cross coupling between counter electrodes and working electrodes according to an embodiment of the present invention. In FIG. 4, there are two counter electrodes 40, 42 and two working electrode 44, 46. Each counter electrode 40, 42 wraps around a working electrode 44, 46 in a U-shaped fashion. A reference electrode 48 may be positioned between the counter electrodes 40, 42. According to this embodiment of the present invention, cross coupling between a first counter electrode 40 and a second working electrode 46 and a second counter electrode 42 and a first working electrode 44 may be minimized. The first and second counter electrodes 40, 42 may be electronically coupled such that the voltage or electric potential of the counter electrodes 40, 42 is equivalent.

In addition, all the sensor electrodes may be electroplated. Electroplating may be accomplished with any of a variety of electroplating materials that are common in the industry, such as, for example, platinum, silver, silver chloride and the like. The electronic circuit may contain plating circuitry that may be used for this purpose. For example, the electronic circuit may contain a plating circuit that is utilized only during the manufacturing process to facilitate electroplating of the electrodes.

Returning to FIG. 1, the sensor electrodes 10 may interface to a data converter 12. The data converter 12 may be any type of analog-to-digital converter suitable for converting an electronic parameter coming from the sensor electrodes 10 into a form suitable for use by the remainder of the electronic circuit. For example, the data converter may convert current to digital data or voltage to digital data. According to an embodiment of the present invention, the data converter may convert current to frequency. A current-to-frequency converter suitable for use in an embodiment of the present invention is disclosed in U.S. Pat. No. 5,917,346, Low Power Current-to-Frequency Converter Circuit For Use In Implantable Sensors, by John C. Gord, assigned to the Alfred E. Mann Foundation, which is incorporated herein by reference.

The counter 14 may be any counter commonly used in the industry such as, for example, a ripple counter. The control logic 16 may be any control logic that facilitates accurate operation of the counter 14. The counter and control logic may operate in a synchronous or asynchronous mode. The counter 14 and control logic 16 may be implemented in a variety of ways, such as, for example, with discrete devices or with a microprocessor.

The line interface 18 may receive information in a variety of forms such as, for example, in pulses, from a remotely located implant unit or other device to which the electronic circuit is interfaced. The line interface 18 may generate data and clock signals for use by other parts of the electronic circuitry from such information. The line interface 18 may also send information in the form of pulses, for example, back to the implant unit or other device to which it is interfaced.

The power rectifier 22 may take power from communication signals incident on the input lines 20 and store such power on a storage device such as, for example, a capacitor. According to embodiments of the present invention, there is no internal energy generating device such as, for example, a battery, resident in the electronic circuit. Power is derived from the communication signals using the power rectifier 22. Thus, the electronic circuit may be used for long term sensing applications since there is no concern for depletion of an energy generating device such as, for example, a battery, within the electronic circuit. A power rectifier circuit suitable for use in an embodiment of the present invention is disclosed in U.S. Pat. No. 5,999,849, Low Power Rectifier Circuit For Implantable Medical Device, by John C. Gord et al, assigned to the Alfred E. Mann Foundation, which is incorporated herein by reference.

Figure 5:
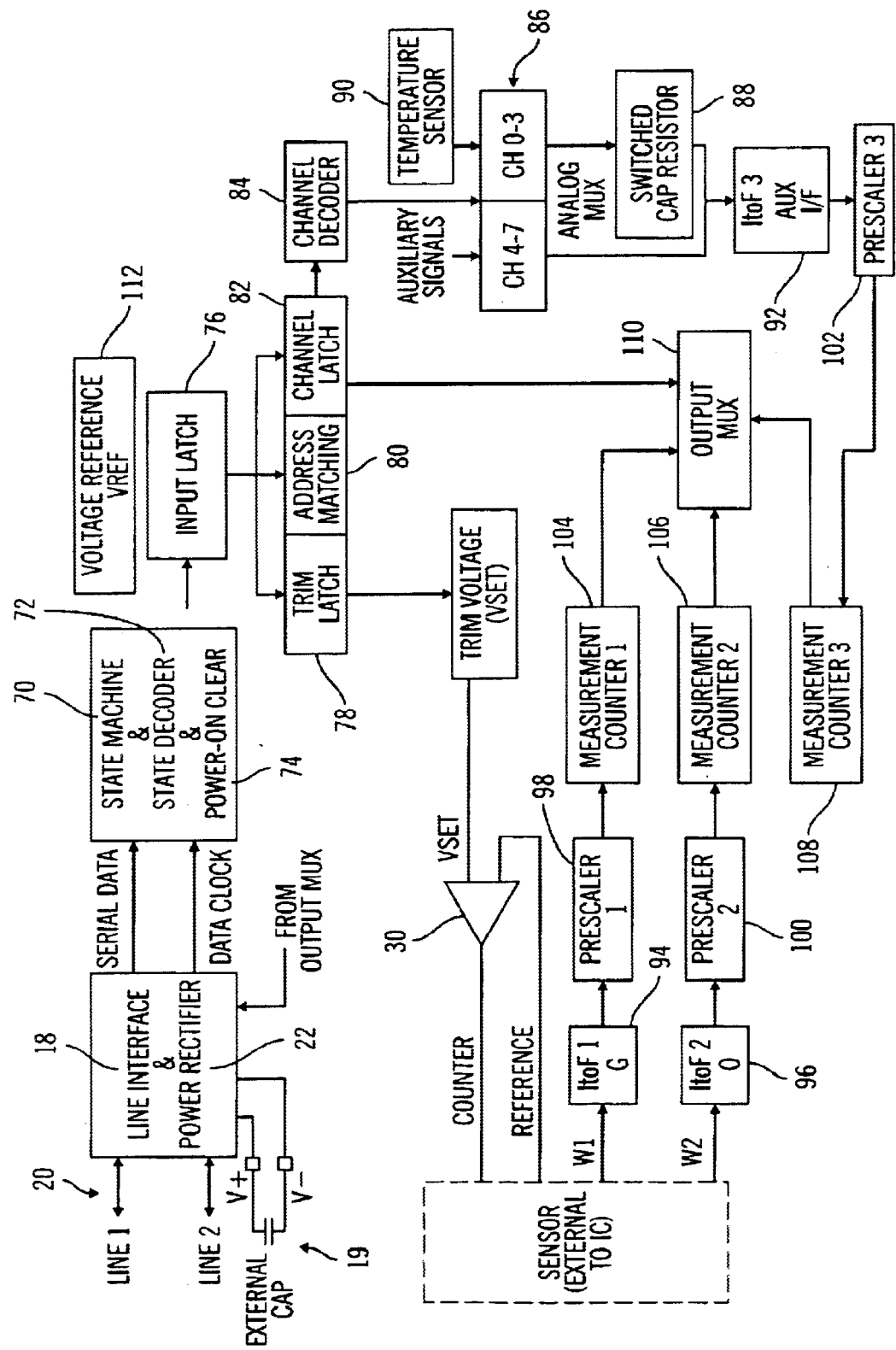
FIG. 5 shows a detailed block diagram of an electronic circuit according to an embodiment of the present invention.

FIG. 5 shows a more detailed block diagram of an electronic circuit according an embodiment of the present invention. Input/output lines 20 connect to a line interface 18 and power rectifier 22 and provide a communications link between the electronic circuit and a remotely located implant unit or other device.

Figure 6:
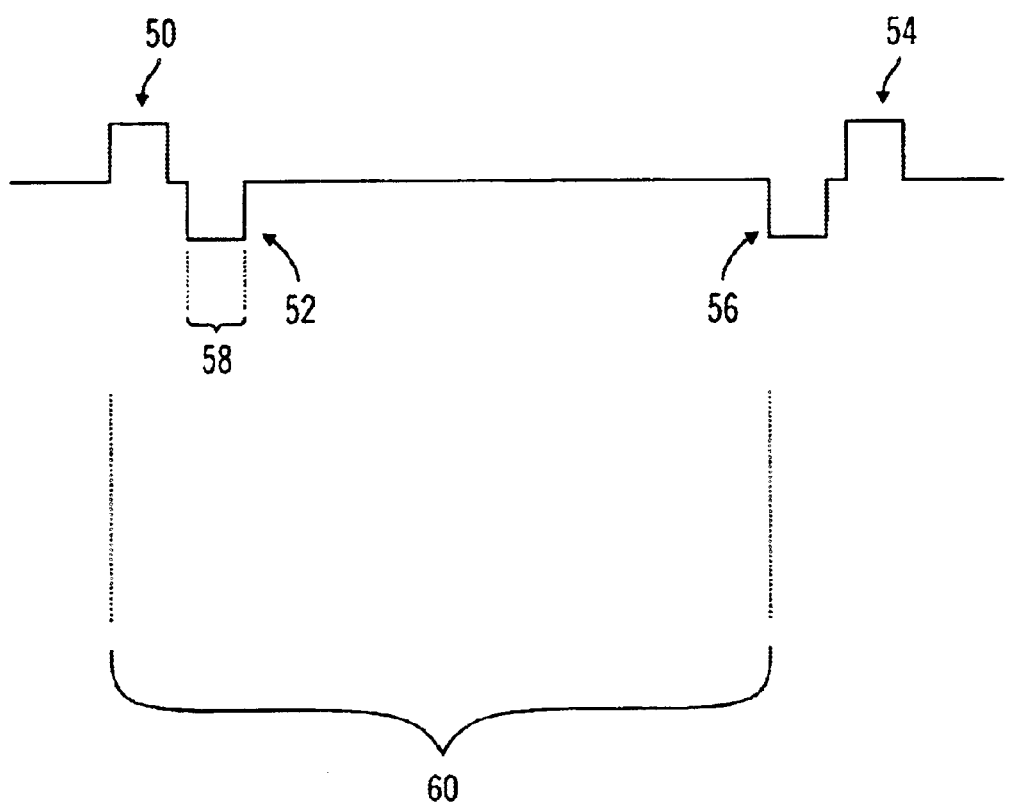
FIG. 6 shows a transmitted pulse waveform according to an embodiment of the present invention.

According to an embodiment of the present invention, a remotely located implant unit or other device may communicate with the electronic circuit using a series of bipolar pulses transmitted across the input/output lines. A transmitted pulse waveform may be seen in FIG. 6. Each bipolar pulse 50, 52, 54, 56 may represent one bit of data from the remotely located implant unit or other device communicating with the electronic circuit. Each bipolar pulse 50, 52, 54, 56 may comprise a positive and a negative level. According to an embodiment of the present invention, a binary one may be designated by a positive level followed by a negative level. A positive level not followed by a negative level may designate a binary zero. According to an embodiment of the present invention, transmit pulse amplitudes may be between 2.3 volts and 3.6 volts. In FIG. 6, a first pulse 50 transmitted is a positive pulse and is followed by a negative pulse. Thus, the pair of pulses 50, 52 indicate a binary one according to an embodiment of the present invention. The second pair of pulses 54, 56 in FIG. 6 is a negative pulse followed by a positive pulse. Thus, according to an embodiment of the present invention, the second pair of pulses 54, 56 represent a binary zero. A zero voltage level may exist between positive and negative pulses. According to an embodiment of the present invention, a pulse width 58 may be approximately 1.9 micro seconds. The pulses may have a pulse repetition rate of 4,096 hertz, corresponding to a period 60 of approximately 244 microseconds. The pulse repetition rate may be adjustable according to the equation 4,096 Hertz/n, where n=1, 2, 3, 4, 5, 6, 7 or 8.

According to an embodiment of the present invention, the electronic circuit may be implemented with a variety of communication delays built in so that the integrity of data transmissions may be increased. For example, according to an embodiment of the present invention, a 152 microsecond delay after receipt of a pair of transmitted pulses may be used for ignoring other pulses on the input/output lines. By implementing such a delay, confusion as to the intended recipient of the pulses may be decreased if, for example, there are a plurality of electronic circuits using the same input/output lines or of the electronic circuit has put its own pulses onto the input/output lines.

Following receipt of data bits by the electronic circuit from the remotely located implant unit or other device, the electronic circuit may respond in a variety of ways depending on the opcode or data received. For example, the electronic circuit may respond by outputting a counter value, a trim setting value, a mode status, a channel setting, an identification number that has been permanently etched onto the circuit, or the like. According to an embodiment of the present invention, the electronic circuit may respond in the form of unipolar pulses. For example, if the response value is a binary one, the electronic circuit may set a logic high using a positive pulse for a duration from between one to ten microseconds, nominally 44 microseconds after the first edge of the bipolar pulse received from the remotely located implant unit or other device. The amplitude of the pulses sent by the electronic device to the remotely located implant unit or other device may be between one volt and 3.6 volts. If the response from the electronic circuit is a binary zero, no pulse may be sent by the electronic circuit to the remotely located implant unit or other device.

Returning to FIG. 5, the input lines 20 may be fed to a power rectifier 22 which uses pulses incident on the input lines 20 to charge a capacitor 19. Electrical charge stored in the capacitor 19 extracted from the communication pulses on the input lines 20 may be used to power the electronic circuit. The capacitor 19 may also act as a low pass filter for the electronic circuit to reduce voltage ripple. According to an embodiment of the present invention, using a pulse width of 2 microseconds every 244 microseconds, the capacitance may be about 0.033 microfarads. Because a capacitor of this size may be too large for an integrated device, if the electronic circuit is fabricated as an integrated circuit, the capacitor 19 may be a discrete capacitor external to the electronic circuit. According to an embodiment of the present invention, the capacitor may be charged to +/−3 volts.

The input lines 20 may also be connected to a line interface 18 which, according to an embodiment of the present invention, may receive information in a form such as, for example, bipolar pulses from a remotely located implant unit or other device. The line interface 18 may also generate data and clock signals and may also send unipolar pulses back to the remotely located implant unit or other device.

A state machine 70 and state decoder 72 may be connected to the line interface 18. Data and clock signals generated by the line interface 18 may be used by the state machine 70 to extract data and to determine the nature of the bipolar pulses received on the input lines 20. The state machine 70 may provide a variety of functions for the electronic circuit. For example, the state machine 70 may generate system clocks, clear counters, check parity and the like. The state machine 70 may also decode opcodes and data. Decoded opcodes may designate a variety of functions such as, for example, latching a new multiplexer channel setting, setting trim values and setting a test mode. The state decoder 72 may be used to decode counter outputs. In addition, the state machine 70 and state decoder 72 may include a power-on clear circuit 74. According to an embodiment of the present invention, the power-on clear circuit 74 may be a typical RC type pulse generation circuit having a 50 picofarad capacitor, a transistor acting as a resistor, and two inverters to square a pulse.

The state machine 70 and state decoder 72 may interface to an input latch 76. According to an embodiment of the present invention, the input latch 76 may be used to latch addresses, opcodes and data used in a command.

The input latch 76 may feed a trim latch 78, an address matching circuit 80 and a channel latch 82. The channel latch 82 may comprise a plurality of latches with data inputs from the input latch 76. The channel latch 82 may be used to control prescalers and multiplexers. The trim latch 78 may also consist of a plurality of latches. Inputs to the trim latch 78 may contain trim setting data. Once latched, the trim setting may be maintained until the next trim setting operation or until a power-on reset occurs.

According to an embodiment of the present invention, trim settings may have secret handshakes. Because trim settings may greatly affect the operation of the electronic circuit, care may be taken to minimize errors when setting trim voltages. For example, the electronic circuit may receive specific commands with no other commands in between before trim voltages are set.

The address matching circuit 80 may be used to verify that instructions and data sent to an electronic circuit are being received by the intended electronic circuit. In applications where multiple sensors, sensor electrodes and sensor electronic circuits are used, the address matching circuit 80 can verify that each electronic circuit receives instructions and data intended for it. For example, in some applications, several electronic circuits may be daisy chained together. Because each electronic circuit may have a unique address, instructions and data sent over a serial bus may be received by each electronic circuit but intended for only one electronic circuit. The address matching circuit 80 will read the address for which the instructions and data are intended and compare that address to the address of the electronic circuit in which the address matching circuit 80 is resident. If the address read by the address matching circuit 80 matches the address of the electronic circuit, the instructions and data will be used by the electronic circuit. If the address read by the address matching circuit 80 does not match the address of the electronic circuit, the instructions and data will be ignored by the electronic circuit.

The channel latch 82 may feed a channel decoder 84. The channel decoder 84 may decode channel bytes from the channel latch 82 into channel select signals. The channel decoder 84 signals may then be used to control an analog multiplexer 86 for the selection of auxiliary signals for measurement. The analog multiplexer 86 may multiplex auxiliary signals to a data converter for measurement. The analog multiplexer 86, according to an embodiment of the present invention, may be an eight channel CMOS multiplexer. If voltage signals are multiplexed out of the analog multiplexer, they may be directed to a switched capacitor resistor 88 for conversion of the voltages to currents, thereby putting the voltages in a form that may be measured by current to frequency converters. Although a discrete resistor or a transistor used as a resistor may be used in place of the switched capacitor resistor 88, the switched capacitor resistor 88 is used because it is generally smaller than other types of resistors and takes up less space in the electronic circuit.

A temperature sensor 90 may be fed into the analog multiplexer 86 providing an output current that is a function of temperature. According to an embodiment of the present invention, nominal output current from the temperature sensor 90 may be 50 nanoamps and may change by 1 nanoamp per degree Celsius. Because some physiological parameter sensing applications are temperature dependent, such as, for example, a glucose oxygen reaction, precise calibration of the electronic circuitry depends on the temperature of the environment in which the electronic circuit is located, such as, for example, the human body. Therefore, the temperature sensor 90 may be included in the electronic circuit to provide proper calibration of the electronic circuit. For example, a patient with a fever may cause a different glucose/oxygen reaction than a patient with a normal body temperature. The temperature sensor 90 may be used to compensate for this difference.

Several current-to-frequency 92, 94, 96 converters may be used in the electronic circuit shown in FIG. 5. Current-to-frequency converters 92, 94, 96 provide an easy method by which to count cycles, consume very low power, automatically average, and make current measurement relatively inexpensive. In addition, current-to-frequency converters 92, 94, 96 are conducive to measuring current through the working electrodes 34 while holding the working electrodes 34 at ground without using a negative power supply. Current passing from the counter electrodes 36 to the working electrodes 34 tends to drive the working electrodes 34 above ground. The current-to-frequency converters 92, 94, 96 emit negative charge packets. By interfacing the working electrodes 34 to the current-to-frequency converters 92, 94, 96, the working electrodes 34 may be maintained at ground. This is because the negative charge packets emitted by the current-to-frequency converters 92, 94, 96 tend to offset the current from the counter electrodes 36 tending to drive the working electrodes 34 above ground.

The current-to-frequency 92, 94, 96 converters may be calibrated in a variety of ways. According to an embodiment of the present invention, the current-to-frequency 92, 94, 96 converters may be calibrated at about 100 counts/sec/nanoamp. The calibration of the current-to-frequency 92, 94, 96 converters may depend on a variety of factors including, without limitation, the length of the counting time and any current-to-frequency conversion factors.

The current-to-frequency converters 92, 94, 96 may feed prescalers 98, 100, 102. The prescalers 98, 100, 102 may be used to modify the output of the current-to-frequency converters 92, 94, 96. For example, the prescalers 98, 100, 102 may simply be divide by 16 circuits that reduces the number of counts seen by the measurement counters 104, 106, 108. In this way, the burden on the measurement counters 104, 106, 108 is minimized and risk of the measurement counters 104, 106, 108 overflowing is reduced. However, the electronic circuit may be designed such that use of the prescalers 98, 100, 102 is optional by setting a flag or other indicator.

The measurement counters 104, 106, 108 may be used to measure the output of the current-to-frequency converters 92, 94, 96 or to measure auxiliary signals. By knowing the count of the frequency output by the current-to-frequency converters 92, 94, 96, the length of the counting time, and any current-to-frequency conversion factors used by the current-to-frequency converters 92, 94, 96, the current generated by the sensor may be calculated. The measurement counters 104, 106, 108 may contain their own multiplexers. The measurement counters 104, 106, 108, or the multiplexers on the measurement counters 104, 106, 108, may feed a general output multiplexer 110 which sends count values to the line interface 18. The line interface 18 may then send these count values back to a remotely located implant unit or other device.

The electronic circuit may also contain a voltage reference 112. The voltage reference 112 may take a variety of forms. For example, the voltage reference 112 may be a band gap reference circuit and may provide bias voltages used to provide known currents to transistors.

The electronic circuit may also contain a variety of other elements. For example, the electronic circuit may contain a test pad used for test purposes. A clock may be fed into the test pad to exercise the counters. The test pad may also be configured as an output so that on-chip voltage references may be measured.

The electronic circuit may also contain variable bias circuitry. In order for the electronic circuit to operate quickly, a significant amount of bias current may be required to drive the transistors included in the circuit. However, there may be extended periods of time when the electronic circuit engages in very little activity. During periods of little activity, the variable bias circuitry may decrease the amount of bias current available to the electronic circuit. In addition, as soon as the voltage on the input lines varies by a threshold amount such as, for example, a volt or so, the variable bias circuitry may increase the amount of bias current available to the electronic circuit so that all of the functions of the electronic circuit may operate quickly. Thus, the variable bias circuitry may provide a dynamically adjustable bias current for the electronic circuit. The variable bias circuitry may anticipate pulses being received on the input lines so that, when the pulses arrive at the electronic circuit, an adequate amount of bias current is available for fast operation of the electronic circuit.

Figure 7:
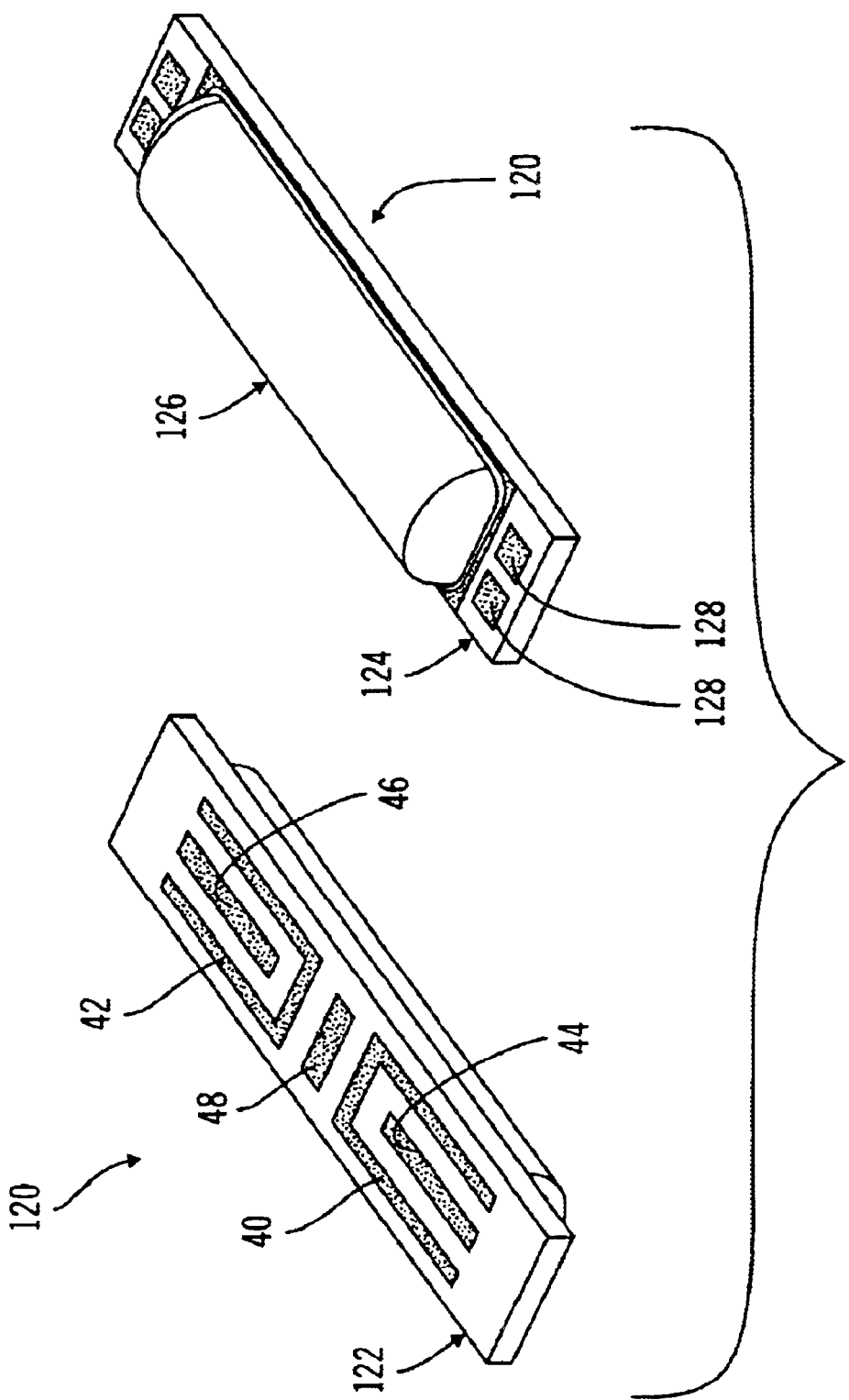
FIG. 7 shows a substrate having a first side which contains an electrode configuration and a second side which contains electronic circuitry according to an embodiment of the present invention.

The electronic circuit may be implemented in a variety of ways. According to an embodiment of the present invention, the electrodes and the circuitry may be affixed to a single substrate. FIG. 7 shows a substrate 120 having two sides, a first side 122 of which contains an electrode configuration and a second side 124 of which contains electronic circuitry. As may be seen in FIG. 7, a first side 122 of the substrate comprises two counter electrode-working electrode pairs 40, 42, 44, 46 on opposite sides of a reference electrode 48. A second side 124 of the substrate comprises electronic circuitry. As shown, the electronic circuitry may be enclosed in a hermetically sealed casing 126, providing a protective housing for the electronic circuitry. This allows the sensor substrate 120 to be inserted into a vascular environment or other environment which may subject the electronic circuitry to fluids. By sealing the electronic circuitry in a hermetically sealed casing 126, the electronic circuitry may operate without risk of short circuiting by the surrounding fluids. Also shown in FIG. 7 are pads 128 to which the input and output lines of the electronic circuitry may be connected.

The electronic circuitry itself may be fabricated in a variety of ways. According to an embodiment of the present invention, the electronic circuitry may be fabricated as an integrated circuit using techniques common in the industry.

Figure 8:
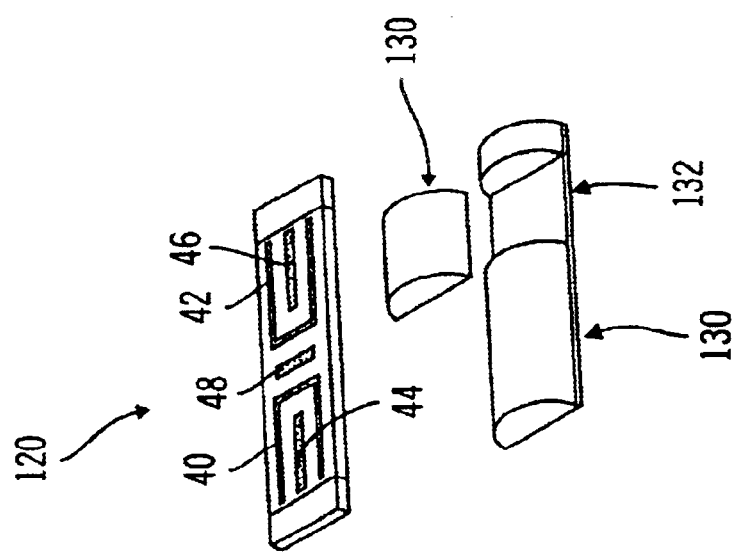
FIG. 8 shows an electrode side of a sensor substrate used with the spacers according to an embodiment of the present invention.

FIG. 8 shows an electrode side of a sensor substrate 120 used with the spacers 130 according to an embodiment of the present invention. The embodiment shown in FIG. 8 may be used for physiological parameter sensing such as, for example, glucose sensing in the human body. The spacer 130 may be placed on top of the electrodes 40, 42, 44, 46, 48. If the spacer 130 is made of silicon, for example, the spacer 130 may pass oxygen but will not pass glucose. A glucose oxidase enzyme may be placed in the indentation 132 of the spacer 130, thereby resting over a second counter electrode-working electrode pair 42, 46. Oxygen passing through the silicon spacer 130 and reacting with a first counter electrode-working electrode pair 40, 44 may be read by the current-to-frequency converters and used to establish a reference amount of oxygen in the blood. Glucose reacting with the glucose oxidase enzyme seated over the second counter electrode-working electrode pair 42, 46 will tend to use up oxygen, leaving less oxygen available for reaction with the second counter electrode-working electrode pair 42, 46. Nonetheless, the remaining amount of oxygen will still react with the second counter electrode-working electrode pair 42, 46, and this value may be read by the current-to-frequency converter to which it is connected. The values out of each current-to-frequency converter may be read and the differing amounts of oxygen may be used to determine the amount of glucose in the blood. The amount of glucose in the blood may be used to automatically deliver insulin to a patient using an implantable pump or other device.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. An electronic circuit for sensing an output of a sensor, the electronic circuit comprising:

a substrate;

at least two electrode pairs formed on a first surface of the substrate for sensing a parameter, each electrode pair having a first electrode and a second electrode, wherein the first electrode of each electrode pair wraps at least partially around the second electrode of its electrode pair; and circuitry for processing the parameter, wherein a layout of the at least two electrode pairs minimizes cross coupling between at least one electrode of a first electrode pair and at least one electrode of a second electrode pair.

2. The electronic circuit of claim 1, wherein the first electrode of each electrode pair wraps around the second electrode of its electrode pair in a U-shaped fashion.

3. The electronic circuit of claim 1, wherein the first electrode of each electrode pair wraps around the second electrode of its electrode pair by surrounding three sides of the second electrode.

4. The electronic circuit of claim 1, further comprising a reference electrode for setting a reference voltage for the at least two electrode pairs.

5. The electronic circuit of claim 4, wherein the reference voltage set on the reference electrode is about 0.5 volts.

6. The electronic circuit of claim 1, wherein the circuitry comprises a line interface for interfacing with input/output lines;

a rectifier in parallel with the line interface;

a counter connected to the line interface; and a data converter connected to the counter and the at least two electrode pairs.

7. The electronic circuit of claim 6, further comprising control logic connected to the counter and the line interface.

8. The electronic circuit of claim 7, wherein the control logic comprises a state machine; and a state decoder connected to the state machine.

9. The electronic circuit of claim 7, wherein the control logic comprises a microprocessor.

10. The electronic circuit of claim 6, wherein the rectifier transfers power from communication pulses to a capacitor.

11. The electronic circuit of claim 10, wherein the capacitor powers the electronic circuit using power stored from the communication pulses.

12. The electronic circuit of claim 6, wherein the data converter is an analog-to-digital converter.

13. The electronic circuit of claim 6, wherein the data converter is a voltage-to-frequency converter.

14. The electronic circuit of claim 6, wherein the data converter is a current-to-frequency converter.

15. The electronic circuit of claim 14, wherein an output of the current-to-frequency converter is scaled using a prescaler before connecting to the counter.

16. electronic circuit of claim 15, wherein the prescaler is a divide-by-16 prescaler.

17. The electronic circuit of claim 6, wherein the circuitry further comprises a temperature sensor for reading a temperature of an environment; and a voltage reference for applying a voltage to a reference electrode.

18. The electronic circuit of claim 6, further comprising switched capacitor circuits for use as resistors in the electronic circuit.

19. The electronic circuit of claim 1, wherein the parameter sensed by the at least two electrode pairs is a physiological parameter.

20. The electronic circuit of claim 19, wherein the physiological parameter sensed is glucose.

21. The electronic circuit of claim 19, wherein the physiological parameter sensed is oxygen.

22. The electronic circuit of claim 1, wherein at least one of the first electrode and the second electrode is electroplated.

23. The electronic circuit of claim 1, wherein the first electrode is coplanar with the second electrode.

24. The electronic circuit of claim 1, wherein the first electrodes of the at least two electrode pairs are electronically coupled to each other.

25. The electronic circuit recited in claim 1, further comprising a spacer covering the at least two electrode pairs.

26. The electronic circuit recited in claim 25, wherein the spacer includes an area for containing a biomolecule such that the biomolecule is located adjacent to at least one of the at least two electrode pairs.

27. The electronic circuit recited in claim 26, wherein the biomolecule is a glucose oxidase enzyme.

28. The electronic circuit recited in claim 26, wherein the spacer comprises a material that is permeable to oxygen and is not permeable to the biomolecule.

29. The electronic circuit recited in claim 1, wherein the first electrodes of each pair have a U-shape including an open end, the at least two electrode pairs being formed on the first surface of the substrate such that the open ends face in opposing directions.

30. The electronic circuit of claim 1, further comprising a reference electrode separating the at least two electrode pairs.

31. The electronic circuit of claim 30, wherein the reference electrode is substantially rectangular.

32. The electronic circuit of claim 1, wherein the reference electrode is disposed substantially perpendicularly to at least one electrode of each of the at least two electrode pairs.

33. An electronic circuit for sensing an output of a sensor, the electronic circuit comprising:

a substrate;

at least two electrode pairs formed on a first surface of the substrate for sensing a parameter, each electrode pair having a first electrode and a second electrode, wherein the first electrode of each electrode pair wraps at least partially around the second electrode of its electrode pair;

circuitry for processing the parameter, and a reference electrode for setting a reference voltage for the at least two electrode pairs, wherein a layout of the first electrode and the second electrode minimizes cross coupling between the first electrode and the second electrode, and wherein the reference electrode is formed between the at least two electrode pairs.

34. An electronic circuit for sensing an output of a sensor, the electronic circuit comprising:

a substrate;

at least two electrode pairs formed on a first surface of the substrate for sensing a parameter, each electrode pair having a first electrode and a second electrode, wherein the first electrode of each electrode pair wraps at least partially around the second electrode of its electrode pair;

circuitry for processing the parameter, and a reference electrode for setting a reference voltage for the at least two electrode pairs, wherein a layout of the first electrode and the second electrode minimizes cross coupling between the first electrode and the second electrode, wherein the reference electrode is disposed between and separates the at least two electrode pairs, and wherein the first electrode of each of the at least two electrode pairs separates the reference electrode and the second electrode of each of the at least two electrode pairs.

35. The electronic circuit of claim 34, wherein the reference electrode is rectangular.

36. The electronic circuit of claim 34, wherein the second electrode is rectangular.

37. The electronic circuit of claim 36, wherein the reference electrode is perpendicular to the second electrode.

38. The electronic circuit of claim 34, wherein the second electrode is disposed within the boundaries of the first electrode.

39. The electronic circuit of claim 38, wherein the second electrode is substantially parallel with at least one leg of the first electrode.

40. The electronic circuit of claim 34, wherein the reference electrode is disposed perpendicularly to the second electrode of each of the at least two electrode pairs.

* * * * *